United States Patent [19]

Hoelderich et al.

[11] Patent Number: 5,079,367
[45] Date of Patent: Jan. 7, 1992

[54] PREPARATION OF 3-HYDROCARBYL SUBSTITUTED PYRIDINES

[75] Inventors: Wolfgang Hoelderich, Frankenthal; Norbert Goetz, Worms; Gerd Fouquet, Neustadt, all of Fed. Rep. of Germany

[73] Assignee: BASF Aktiengesellschaft, Ludwigshafen, Fed. Rep. of Germany

[21] Appl. No.: 442,725

[22] Filed: Nov. 29, 1989

Related U.S. Application Data

[63] Continuation of Ser. No. 105,541, Oct. 9, 1987, abandoned.

[30] Foreign Application Priority Data

Oct. 8, 1986 [DE] Fed. Rep. of Germany ....... 3634259

[51] Int. Cl.$^5$ ................ C07D 213/06; C07D 213/16
[52] U.S. Cl. ..................................... 546/251; 546/250
[58] Field of Search ............................... 546/250, 251

[56] References Cited

U.S. PATENT DOCUMENTS

| | | | |
|---|---|---|---|
| 4,616,098 | 10/1986 | Hoelderich et al. | 585/640 |
| 4,675,410 | 6/1987 | Feitler et al. | 546/251 |
| 4,692,424 | 9/1987 | Le Van Mao | 502/68 |

FOREIGN PATENT DOCUMENTS

| | | |
|---|---|---|
| 0131887 | 1/1985 | European Pat. Off. |
| 0232182 | 8/1987 | European Pat. Off. |
| 2703070 | 7/1978 | Fed. Rep. of Germany |

*Primary Examiner*—Alan L. Rotman
*Attorney, Agent, or Firm*—Keil & Weinkauf

[57] ABSTRACT

Substituted pyridines of the formula

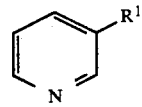

where $R^1$ is alkyl of 1 to 20 carbon atoms, cycloalkyl, aryl or aralkyl, are prepared by reacting a mixture of acrolein and alkanals of the formula

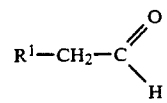

with ammonia in the presence of zeolites as catalysts.

3 Claims, No Drawings

PREPARATION OF 3-HYDROCARBYL SUBSTITUTED PYRIDINES

This application is a continuation of application Ser. No. 105,541 filed on Oct. 9, 1987.

The present invention relates to a process for preparing a substituted pyridine by catalytic reaction of a mixture of acrolein and an alkanal with ammonia in the presence of a zeolite.

It is known that the reaction of acrolein with ammonia in the gas phase in the presence of catalysts produces 3-methylpyridine. The catalysts used are compounds which are composed of the elements aluminum, fluorine and oxygen, which have been pretreated with oxygen at from 550° to 1200° C. and which contain in addition one or more elements of the second, third or fourth group of the periodic table (German Laid-Open Application DOS 2,151,417) or two or more elements of the second, fourth, fifth or sixth group of the periodic table (German Laid-Open Application DOS 2,224,160) or one or more elements of the second main group of the periodic table (German Laid-Open Application DOS 2,239,801). If the reaction is carried out in a fluidized bed, it is also known to feed the acrolein into the fluidized bed separately from the ammonia. The disadvantage with these processes is that not only 3-methylpyridine but also pyridine is produced in a considerable amount.

3-Methylpyridine is also obtained in moderate yields by reacting mixtures of acrolein and propionaldehyde with ammonia in the presence of catalysts which contain aluminum oxides and silicon oxides. By using finely divided aluminum silicates, the yield of 3-methylpyridine can be somewhat increased (German Laid-Open Application DOS 2,703,070).

U.S. Pat. No. 4,220,783 describes a process for preparing pyridine and picoline over aluminosilicate zeolite ZSM 5 by reacting $C_2$–$C_4$-aldehydes or $C_3$–$C_5$-ketones with ammonia in the presence of methanol or water. The catalyst deactivates very quickly. The yields are unsatisfactory.

EP 131,887 discloses that acidic aluminosilicate zeolites of the pentasil type with a constraint index of from 1 to 12 produce better results in the preparation of alkylpyridines in a fluidized bed than in a fixed bed. In the reaction of acetaldehyde with formaldehyde, the total yield of the pyridines obtained can be as high as 89.8% with the pyridine/β-picoline ratio being equal to 2:1. The reaction temperature is above 450° C., and the catalyst needs to be regenerated after only 4 hours.

It is an object of the present invention to synthesize a substituted pyridine selectively from readily available starting materials without producing major quantities of pyridine at the same time.

We have found that this object is achieved with a simple process for preparing a substituted pyridine of the formula (I)

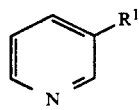
(I)

where $R^1$ is alkyl of 1 to 20 carbon atoms, cycloalkyl, aryl or aralkyl, by reacting a mixture of acrolein and an alkanal of the formula (II)

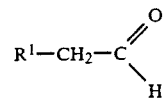
(II)

where $R^1$ has the above meanings, with ammonia in the presence of a zeolite as catalyst.

The reaction is preferably carried out in the gas phase at from 100° to 500° C. According to the invention, a mixture of acrolein and an alkanal of the formula (II) is reacted. Suitable alkanals are for example propionaldehyde, butyraldehyde, isobutyraldehyde, pentanal, hexanal, octanal, phenylacetaldehyde, 3-phenylpropanal, cyclohexylacetaldehyde or cyclopentylacetaldehyde.

The reaction according to the invention can be represented for example for the case of the preparation of 3-ethylpyridine by the following formula equation:

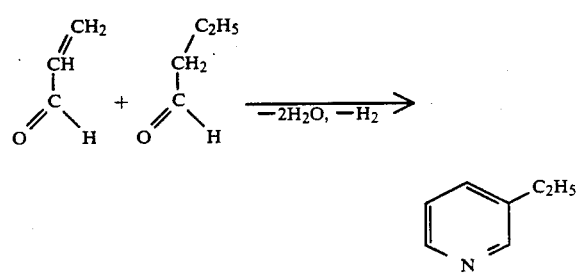

Performing the reaction according to the invention in the presence of a zeolite is surprising inasmuch as zeolites normally have cracking properties which, in the reaction of relatively long-chain alkanals, would be increasingly expected to produce chain breakage.

The catalyst used for the process according to the invention advantageously is a zeolite in the acidic form. Zeolites are crystalline aluminosilicates which have a highly ordered structure with a rigid three-dimensional network of $SiO_4$ and $AlO_4$ tetrahedra linked by common oxygen atoms. The ratio of the Si and Al atoms:oxygen is 1:2. The electrovalence of the aluminum-containing tetrahedra is balanced by the inclusion in the crystal of cations, for example an alkali metal or hydrogen ion. Cation exchange is possible. The spaces between the tetrahedra are occupied by water molecules prior to dehydration through drying or calcination.

In the zeolites, the aluminum in the lattice can be replaced by other elements such as B, Ga, Fe, Cr, V, As, Sb, Bi or Be or mixtures thereof, or the silicon can be replaced by a tetravalent element such as Ge, Ti, Zr or Hf.

According to their structure, zeolites are divided into various groups. For instance, the zeolite structure in the mordenite group is formed by tetrahedra arranged in chains and in the chabasite group by tetrahedra arranged in layers, while in the faujasite group the tetrahedra form polyhedra, for example in the form of a cuboctahedron which is composed of tetragons and hexagons. Depending on the way the cuboctahedra are linked, which produces differently sized voids and pores, zeolites are classed as type A, L, X or Y.

Catalysts suitable for the process according to the invention are zeolites from the mordenite group or narrow-pored zeolites of the erionite or chabasite type or zeolites of the faujasite type, for example Y-, X- or L-zeolites. This group of zeolites also includes the ultrastable zeolites of the faujasite type, ie. dealuminized zeolites. Methods for preparing such zeolites have repeatedly been described.

Zeolites of the pentasil type are particularly advantageous. Their common feature is a pentagon composed of $SiO_4$ tetrahedra. They are characterized by a high $SiO_2/Al_2O_3$ ratio and by pore sizes between those of the zeolites of type A and those of type X or Y.

These zeolites can have different chemical compositions. They can be aluminosilicate, borosilicate or iron, beryllium, gallium, chromium, arsenic, antimony or bismuth silicate zeolites or mixtures thereof and alumino-germanate, borogermanate and gallium or iron germanate zeolites or mixtures thereof. Particularly suitable for the process according to the invention are the aluminosilicate, borosilicate and iron silicate zeolites of the pentasil type.

The aluminosilicate zeolite is prepared for example from an aluminum compound, preferably $Al(OH)_3$ or $Al_2(SO_4)_3$, and a silicon component, preferably finely divided silicon dioxide, in an aqueous amine solution, in particular in polyamines such as 1,6-hexanediamine or 1,3-propanediamine or triethylenetetramine solution, in the presence or in particular in the absence of alkali or alkaline earth metal at from 100° to 220° C. under autogenous pressure. This also includes the isotactic zeolites described in EP 34,727 and EP 46,504. The aluminosilicate zeolites obtained have an $SiO_2/Al_2O_3$ ratio of from 10 to 40,000, depending on the mixing ratio of the starting materials. These aluminosilicate zeolites of the pentasil type can also be synthesized in an ether medium such as ciethylene glycol dimethyl ether, in an alcohol medium such as methanol or 1,4-butanediol, or in water.

The high-silicon zeolites usable according to the invention ($SiO_2/Al_2O_3 \geq 10$) also include the various ZSM types, ferrierite, Nu-1 and Silicalit ®.

Borosilicate zeolites can be synthesized under autogenous pressure, for example at from 90° to 200° C., by reacting a boron compound, for example $H_3BO_3$, with a silicon compound, preferably finely divided silicon dioxide, in an aqueous amine solution, in particular in 1,6-hexanediamine, 1,3-propanediamine or triethylenetetramine solution, in the presence or in particular in the absence of alkali or alkaline earth metal. They also include the isotactic zeolites described in EP 34,727 and EP 46,504. These borosilicate zeolites can also be prepared by carrying out the reaction not only in aqueous amine solution but alternatively in an ether solution, for example diethylene glycol dimethyl ether, or in an alcohol solution, for example 1,6-hexanediol.

The iron silicate zeolite is obtained for example from an iron compound, preferably $Fe_2(SO_4)_3$, and a silicon compound, preferably finely divided silicon dioxide, in an aqueous amine solution, in particular 1,6-hexanediamine, in the presence or absence of alkali or alkaline earth metal at from 100° to 200° C. under autogenous pressure.

The aluminosilicate, borosilicate and iron silicate zeolites thus prepared, after they have been isolated, dried at from 100° to 160° C., preferably at 110° C., and calcination at from 450° to 550° C., preferably at 500° C., can be combined with a binder in a ratio of from 90:10 to 40:60% by weight and molded into extrudates or tablets. Suitable binders are various aluminum oxides, preferably boehmite, amorphous aluminosilicates having an $SiO_2/Al_2O_3$ ratio of from 25:75 to 90:5, preferably 75:25, silicon dioxide, preferably finely divided $SiO_2$, mixtures of finely divided $SiO_2$ and finely divided $Al_2O_3$, $TiO_2$, $ZrO_2$, and clay. After molding, the extrudates or tablets are dried at 110° C. for 16 hours and calcined at 500° C. in 16 hours.

It is also possible to obtain advantageous catalysts by molding the isolated aluminosilicate or borosilicate zeolite immediately after drying and subjecting it to calcination only after the molding. The aluminosilicate and borosilicate zeolites prepared can be used in the pure form, without binder, as extrudates or tablets, the extrusion or peptization aids used being for example ethylcellulose, stearic acid, potato starch, formic acid, oxalic acid, acetic acid, nitric acid, ammonia, amines, silicoesters and graphite or mixtures thereof.

If the zeolite, on account of its manner of preparation, is present not in the catalytically active, acidic H-form but, for example, in the Na-form, it can be completely or partially converted into the desired H-form by ion exchange, for example with ammonium ions and subsequent calcination, or by treatment with acids.

Should the zeolitic catalyst used according to the invention undergo deactivation due to coking, it is advisable to regenerate the zeolite by burning off the coke deposit with air or with an air/$N_2$ mixture at from 400° to 550° C., preferably at 500° C. This restores the initial activity level of the zeolite.

By precoking it is possible to set the activity of the catalyst for optimum selectivity in respect of the desired reaction product.

To obtain a high selectivity, high conversions and long times on stream, it is advantageous to modify the zeolites. A suitable method of modifying the catalysts comprises for example doping the shaped or unshaped zeolite with metal salts by ion exchange or impregnation. The metals used are alkali metals such as Li, Cs or K, alkaline earth metals such as Mg, Ca or Sr, metals of main groups III, IV and V, such as Al, Ga, Ge, Sn, Pb or Bi, transition metals of subgroups IV–VIII, such as Ti, Zr, V, Nb, Cr, Mo, W, Mn, Re, Fe, Ru, Os, Co, Rh, Sr, Ni, Pd or Pt, transition metals of secondary groups I or II, such as Cu, Ag or Zn, and rare earth metals such as La, Ce, Pr, Nd, Er, Yb or U.

Advantageously, doping is carried out by introducing the molded zeolite into a riser pipe and passing an aqueous or ammoniacal solution of a halide or nitrate of one of the abovementioned metals over it at from 20° to 100° C. Such an ion exchange can take place with the hydrogen, ammonium, or alkali metal form of the zeolite. Another way of applying metal to the zeolite comprises impregnating the zeolitic material with, for example, a halide, nitrate or oxide of one of the above-mentioned metals in aqueous, alcoholic or ammoniacal solution. Both ion exchange and impregnation are followed by at least a drying step, optionally by repeated calcination.

A possible embodiment comprises for example dissolving solving $Cu(NO_3)_2 \times 3$ $H_2O$ or $Ni(NO_3)_2 \times 6$ $H_2O$ or $Ce(NO_3)_3 \times 6$ $H_2O$ or $La(NO_3)_2 \times 6$ $H_2O$ or $Cs_2CO_3$ in water and impregnating the molded or unmolded zeolite with this solution for a certain period, for example 30 minutes. Any supernatant solution is stripped of water in a rotary evaporator. The impregnated zeolite is then dried at about 150° C. and calcined at about 550° C. This impregnating step can be carried out repeatedly in succession until the desired metal content is obtained.

It is also possible to prepare an aqueous $Ni(NO_3)_2$ solution or ammoniacal $Pd(NO_3)_2$ solution and to suspend the pure pulverulent zeolite therein at from 40° to 100° C. by stirring for about 24 hours. After filtration, drying at about 150° C. and calcination at about 500° C., the zeolitic material thus obtained can be further processed with or without binders into extrudates, pellets or fluidizable material.

An ion exchange on the zeolite present in the H-form or ammonium form or alkali metal form can be carried out by introducing the zeolite in extruded or pellet form into a column and for example passing an aqueous Ni($NO_3$)$_2$ solution or ammoniacal Pd($NO_3$)$_2$ solution over it in a recycle loop and at a slightly elevated temperature of from 30° to 80° C. for from 15 to 20 hours. This is followed by washing out with water, drying at about 150° C. and calcination at about 550° C. With some metal-doped zeolites, for example Pd-, Cu- or Ni-doped zeolites, an aftertreatment with hydrogen is advantageous.

A further method of modifying the zeolite comprises treating the zeolitic material, which may be in molded or unmolded form, with an acid such as hydrochloric acid, hydrofluoric acid or phosphoric acid and/or steam, advantageously, for example, by treating the zeolite in pulverulent form with 1N phosphoric acid at 80° C. for 1 hour and then washing with water and drying at 110° C. for 16 hours and calcining at 500° C. in 20 hours. Alternatively, before or after being molded together with a binder, the zeolite is treated for example at from 60° to 80° C. with from 3 to 25% strength by weight, in particular from 12 to 20% strength by weight, aqueous hydrochloric acid for from 1 to 3 hours. Afterwards, the zeolite thus treated is washed with water, dried and calcined at from 400° C. to 500° C.

In a particular embodiment, the acid treatment comprises treating the zeolitic material, before it is molded, with hydrofluoric acid, generally in the form of 0.001N to 2N, preferably 0.05N to 0.5N hydrofluoric acid, at an elevated temperature, for example by heating under reflux for, in general, from 0.5 to 5, preferably from 1 to 3, hours. After the zeolitic material has been isolated, for example by filtering and washing, it is advantageously dried, for example at from 100° to 160° C., and calcined, in general at from 450° C. to 600° C. In a further preferred form of the acid treatment, the zeolitic material, after it has been molded together with a binder, is treated at an elevated temperature, advantageously at from 50° to 90° C., preferably at from 60° to 80° C., for from 0.5 to 5 hours with, preferably, from 12 to 20% strength by weight hydrochloric acid. Expediently, the zeolitic material is subsequently washed, dried at from 100° to 160° C. and calcined at from 450° to 600° C. An HF treatment can also be followed by an HCl treatment.

The catalysts described here can optionally be used in the form of from 2 to 4 mm extrudates or as tablets from 3 to 5 mm in diameter or as chips having particle sizes of from 0.1 to 0.5 mm, or in a fluidizable form.

The reaction is advantageously carried out with a molar ratio of acrolein:alkanal:$NH_3$ of 1:1-5:1-10, in particular 1:1-2:1-5. In general, the reaction is carried out in the gas phase at from 100° to 500° C., advantageously at from 150° to 450° C., in particular at from 200° to 400° C., under from 0.1 to 100 bar, in particular under from 0.5 to 10 bar. In the gas phase, the catalyst is advantageously operated at a weight hourly space velocity (WHSV) of from 0.1 to 20, in particular of from 1 to 90, g of acrolein and alkanal mixture per g of catalyst per hour. The gas phase reaction can be carried out in a fixed bed or in a fluidized bed. It is also possible to carry out the reaction in the liquid phase (by the suspension, trickle-bed or liquid phase procedure) at from 50° to 200° C. The reaction can be carried out continuously or batchwise.

Involatile or solid starting materials are expediently used in dissolved form, for example in solution in THF, toluene or petroleum ether. In general, the starting material can be diluted with a solvent or an inert gas such as $N_2$, Ar or $H_2O$ vapor. It is advisable to carry out this reaction in the presence of oxygen.

The end products are isolated from the reaction mixture in a conventional manner, for example by distillation; unconverted starting mixture may be recycled into the reaction.

The substituted pyridines obtainable by the process according to the invention have many uses as intermediates, for example for dyes, pharmaceuticals or pesticides, and as solvents.

EXAMPLES 1 TO 40

The reaction is carried out in the gas phase in a tubular reactor (helix, internal diameter 0.6 cm, length 90 cm) under isothermal conditions for not less than 6 hours. The reaction products are separated off and characterized in a conventional manner. The reaction products and starting materials are quantitatively determined by gas chromatography in a conventional manner.

The examples are carried out using the following catalysts:

Catalyst A

A borosilicate zeolite of the pentasil type is prepared in a hydrothermal synthesis from 640 g of finely divided $SiO_2$, 122 g of $H_3BO_3$ and 8000 g of an aqueous 1,6-hexanediamine solution (mixture 50:50% by weight) at 170° C. under autogenous pressure in a stirred autoclave. After filtering and washing, the crystalline reaction product is dried at 100° C. for 24 hours and calcined at 500° C. in 24 hours. This borosilicate zeolite comprises 94.2% by weight of $SiO_2$ and 2.3% by weight of $B_2O_3$.

This material is molded with boehmite in a weight ratio of 60:40 into 2 mm extrudates which are dried at 110° C. for 16 hours and calcined at 500° C. in 24 hours.

Catalyst B

An aluminosilicate zeolite of the pentasil type is prepared under hydrothermal conditions and autogenous pressure and at 150° C. from 65 g of finely divided $SiO_2$, and 20.3 g of $Al_2(SO_4)_3 \times 18\ H_2O$ in 1 kg of an aqueous 1,6-hexanediamine solution (mixture 50:50% by weight) in a stirred autoclave. After filtering and washing, the crystalline reaction product is dried at 110° C. for 24 hours and calcined at 500° C. in 24 hours. This aluminosilicate zeolite contains 91.6% by weight of $SiO_2$ and 4.6% by weight of $Al_2O$. The catalyst is obtained by molding with boehmite in a weight ratio of 60:40 into 2 mm extrudates, drying at 110° C. for 16 hours and calcination at 500° C. in 24 hours.

Catalyst C

Catalyst B is impregnated with an aqueous La($NO_3$)$_3$ solution, dried at 130° C. for 2 hours and calcined at 540° C. in 2 hours. The La content is 3.2% by weight.

Catalyst D

Catalyst B is impregnated with an aqueous $La(NO_3)_3$ solution, dried at 103° C. for 2 hours and calcined at 540° C. in 2 hours. The La content is 3.25% by weight.

Catalyst E 100 g of the borosilicate zeolite used for catalyst A are treated at 90° C. with 280 ml of 0.1N HF for 2 hours, filtered off and dried at 160° C. This product is molded with amorphous aluminosilicate (25% by weight of $Al_2O_3$ and 75% by weight of $SiO_2$) in a weight ratio of 60:40 into 2 mm extrudates, which are dried at 110° C. for 16 hours and calcined at 500° C. in 16 hours.

Catalyst F

Catalyst A is impregnated with aqueous $Co(NO_3)_2$ solution, dried at 130° C. for 2 hours and calcined at 540° C. in 2 hours. The Co content is 3.2% by weight.

Catalyst G

Catalyst A is impregnated with aqueous $Ce(NO_3)_3$ solution, dried at 130° C. for 2 hours and calcined at 540° C. in 2 hours. The Ce content is 2.5% by weight.

Catalyst H

Catalyst H is obtained by molding the alumino-silicate zeolite of catalyst B with a molding aid, and drying at 110° C. for 16 hours and calcining at 500° C. in 24 hours and then impregnating with aqueous $Ce(NO_3)_3$ solution, drying at 130° C. for 2 hours and calcining at 540° C. for 2 hours. The Ce content is 3.4% by weight.

Catalyst I

49% by weight of Baylith ® ( ® registered trademark) are molded with 21% by weight of amorphous aluminosilicate (45% by weight of $Al_2O_3$ and 55% by weight of $SiO_2$), 20% by weight of $MoO_3$ and 10% by weight of NiO into extrudates.

Catalyst J

Commercially available NaY zeolite is molded with boehmite in a weight ratio of 60:40 into 2 mm extrudates, dried at 110° C. for 16 hours and calcined at 540° C. in 24 hours. These extrudates are ion exchanged at 80° C. with a 20% strength aqueous $La(NO_3)_2$ solution in the course of 2 hours. After drying at 100° C. and calcination at 500° C. the La content should be 7.1% by weight and the Na content 1.1% by weight. The ion exchange treatment can be repeated after intermediate calcination until the above La and Na contents are established.

Catalyst K

An aluminosilicate zeolite is prepared as described in the case of catalyst B, except that the 1,6-hexanediamine is replaced by an aqueous solution of 1,3-diaminopropane. The powder dried at 140° C. and calcined at 500° C. in 24 hours contains 89.9% by weight of $SiO_2$ and 4.0% by weight of $Al_2O_3$. This powder is refluxed for 1 hour with 0.1N HF. After washing with $H_2O$, drying at 110° C. and calcination at 500° C. in 5 hours, the alumino-silicate zeolite thus treated is molded with amorphous aluminosilicate (75% by weight of $SiO_2$, 25% by weight of $Al_2O_3$) in a weight ratio of 60:40 into 3 mm extrudates, which are dried at 110° C. and calcined at 500° C. in 16 hours.

Catalyst L

Catalyst L is prepared in the same way as catalyst M, except that the binder used is boehmite in place of amorphous aluminosilicate.

Catalyst M

Catalyst B is impregnated with an aqueous $RhCl_3$ solution, dried at 130° C. for 2 hours and calcined at 540° C. in 2 hours. The Rh content is 2.84% by weight.

Catalyst N

Catalyst A is impregnated with an aqueous $Co(NO_3)_2$ solution and an aqueous $Ca(NO_3)_2$ solution, dried at 130° C. for 2 hours and calcined at 540° C. in 2 hours. The Co content is 1.1% by weight and the Ca content 0.1% by weight.

The experimental results and the reaction conditions are summarized in the tables below.

TABLE 1

| | Acrolein:n-butanal:$NH_3$ = 1:1:3 molar | | | | | | | | | |
|---|---|---|---|---|---|---|---|---|---|---|
| Example | 1 | 2 | 3 | 4 | 5 | 6 | 7 | 8 | 9 | 10 |
| Catalyst | A | B | B | B | C | E | E | D | I | J |
| Temperature | 400° C. | 350° C. | 400° C. | 400° C. | 400° C. | 350° C. | 400° C. | 400° C. | 400° C. | 400° C. |
| WHSV | 3 h$^{-1}$ | 3 h$^{-1}$ | 3 h$^{-1}$ | 1,5 h$^{-1}$ | 3 h$^{-1}$ | 3 h$^{-1}$ | 3 h$^{-1}$ | 3 h$^{-1}$ | 3 h$^{-1}$ | 3 h$^{-1}$ |
| Conversion %$^{1)}$ | 100 | 100 | 100 | 100 | 100 | 100 | 100 | 100 | 100 | 100 |
| Selectivity % | | | | | | | | | | |
| 3-Ethylpyridine | 70.0 | 68.6 | 65.7 | 67.7 | 67.6 | 67.2 | 72.0 | 67.9 | 68.0 | 71.4 |
| β-Picoline | 15.6 | 15.1 | 14.4 | 16.5 | 16.6 | 15.1 | 15.4 | 16.2 | 10.7 | 16.4 |

1) conversion both of acrolein and n-butanal

TABLE 2

| | Acrolein:n-hexanal:$NH_3$ = 1:1:3 molar | | | | |
|---|---|---|---|---|---|
| Example | 11 | 12 | 13 | 14 | 15 |
| Catalyst | B | B | E | E | J |
| Temperature | 350° C. | 400° C. | 350° C. | 350° C. | 400° C. |
| WHSV | 3 h$^{-1}$ | 3 h$^{-1}$ | 3 h$^{-1}$ | 6 h$^{-1}$ | 3 h$^{-1}$ |
| Conversion % | 100 | 100 | 100 | 100 | 100 |
| Selectivity % | | | | | |
| 3-Butylpyridine | 76.8 | 69.0 | 76.2 | 77.6 | 74.1 |

TABLE 2-continued

| | Acrolein:n-hexanal:NH₃ = 1:1:3 molar | | | | |
|---|---|---|---|---|---|
| Example | 11 | 12 | 13 | 14 | 15 |
| β-Picoline | 12.2 | 14.7 | 9.7 | 12.8 | 14.0 |

1) conversion both of acrolein and n-hexanal

TABLE 3

| | Acrolein:octanal:NH₃ = 1:1:3 molar | | | | | |
|---|---|---|---|---|---|---|
| Example | 16 | 17 | 18 | 19 | 20 | 21 |
| Catalyst | E | E | E | J | B | F |
| Temperature | 400° C. | 450° C. | 400° C. | 400° C. | 400° C. | 400° C. |
| WHSV | 3 h⁻¹ | 3 h⁻¹ | 1,5 h⁻¹ | 3 h⁻¹ | 3 h⁻¹ | 3 h⁻¹ |
| Conversion % | 100 | 100 | 100 | 100 | 100 | 100 |
| Selectivity % | | | | | | |
| 3-Hexylpyridine | 90.1 | 79.9 | 87.6 | 80.1 | 74.0 | 80.2 |
| β-Picoline | 5.2 | 10.2 | 5.5 | 11.2 | 12.9 | 10.2 |
| Example | 22 | 23 | 24 | 25 | 26 | 27 |
| Catalyst | G | H | K | L | M | N |
| Temperature | 400° C. | 400° C. | 400° C. | 400° C. | 400° C. | 400° C. |
| WHSV | 3 h⁻¹ | 3 h⁻¹ | 3 h⁻¹ | 3 h⁻¹ | 3 h⁻¹ | 3 h⁻¹ |
| Conversion % | 100 | 100 | 100 | 100 | 100 | 100 |
| Selectivity % | | | | | | |
| 3-Hexylpyridine | 81.8 | 81.4 | 85.6 | 82.2 | 88.7 | 79.5 |
| β-Picoline | 8.9 | 9.9 | 5.7 | 8.6 | 7.4 | 8.1 |

1) conversion both of acrolein and n-octanal

TABLE 4

| | Acrolein:phenylacetaldehyde:NH₃ = 1:1:3 molar[1] | | | | |
|---|---|---|---|---|---|
| Example | 28 | 29 | 30 | 31 | 32 |
| Catalyst | A | D | B | E | J |
| Temperature | 300° C. | 300° C. | 300° C. | 300° C. | 300° C. |
| WHSV | 3 h⁻¹ | 3 h⁻¹ | 3 h⁻¹ | 3 h⁻¹ | 3 h⁻¹ |
| Conversion % | 100 | 100 | 100 | 100 | 100 |
| Selectivity % 3-Phenylpyridine | 88.9 | 87.1 | 84.0 | 86.0 | 86.6 |

[1] Mixture of acrolein and phenylacetaldehyde dissolved in THF 50 g:50 g
2) Conversion both of acrolein and phenylacetaldehyde

TABLE 5

| | Acrolein:3-phenylpropanal:NH₃ = 1:1:3 molar[1] | | | | |
|---|---|---|---|---|---|
| Example | 33 | 34 | 35 | 36 | 37 |
| Catalyst | A | B | D | E | J |
| Temperature | 300° C. | 300° C. | 300° C. | 300° C. | 300° C. |
| WHSV | 3 h⁻¹ | 3 h⁻¹ | 3 h⁻¹ | 3 h⁻¹ | 3 h⁻¹ |
| Conversion % | 100 | 100 | 100 | 100 | 100 |
| Selectivity % 3-Benzylpyridine | 86.3 | 83.1 | 84.7 | 89.7 | 90.2 |

[1] Mixture of acrolein and 3-phenylpropanal dissolved in THF 50 g:50 g
2) Conversion both of acrolein and 3-phenylpropanal

TABLE 6

| | Acrolein:n-propanal:NH₃ = 1:1:3 molar | | |
|---|---|---|---|
| Example | 38 | 39 | 40 |
| Catalyst | A | B | E |
| Temperature | 400° C. | 400° C. | 400° C. |
| WHSV | 3 h⁻¹ | 3 h⁻¹ | 3 h⁻¹ |
| Conversion % | 100 | 100 | 100 |
| Selectivity % β-Picolin | 87.2 | 89.3 | 91.0 |

1) Conversion both of acrolein and n-propanal

EXAMPLE 41

In a long-term test, a mixture of acrolein and n-octanal with ammonia in a molar ratio of 1:1:3 was reacted over catalyst E at 400° C. with a WHSV of 3 h⁻¹ in the reactor described above. All the acrolein and n-octanal was converted in 48 hours. No activity loss was found. The selectivity with respect to hexylpyridine and β-picoline was on average 93%.

We claim:
1. A process for preparing a substituted pyridine of the formula (I)

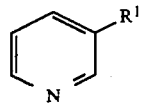 (I)

where $R^1$ is alkyl of 1 to 20 carbon atoms, cyclopentyl, cyclohexyl, phenyl or phenylalkyl with 1-4 carbon atoms in the alkyl which process comprises: reacting with a mixture of acrolein and an aklanal of the formula (II)

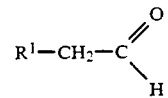 (II)

where $R^1$ has the above meanings, with ammonia, wherein the molar ratio of acrolein:alkanal:$NH^3$ is about 1:1-2:1-5, in the presence of a borosilicate or aluminosilicate zeolite catalyst of the pentasil type, wherein the catalyst is either doped with an alkali metal, alkaline earth metal, transition metal or rare earth or treated with an acid.

2. The process of claim 1, wherein the alkanal of the formula II is selected from the group consisting of propionaldehyde, butyraldehyde, isobutyraldehyde, pentanal, hexanal, octanal, phenylacetaldehyde, 3-phenylpropanal, cyclohexylacetaldehyde and cyclopentylacetaldehyde.

3. The process of claim 2, wherein the substituted pyridine of the formula (I) constitutes at least 65% of the reaction product of the process.

* * * * *

UNITED STATES PATENT AND TRADEMARK OFFICE
CERTIFICATE OF CORRECTION

PATENT NO. : 5,079,367
DATED : Jan, 7, 1992
INVENTOR(S) : Wolfgang HOELDERICH It is certified that error appears in the above-identified patent and that said Letters Patent is hereby corrected as shown below:

IN THE CLAIMS:

Claim 1, column 11, line 20

"with" should be omitted

"aklanal" should read --alkanal--

Signed and Sealed this

Twentieth Day of April, 1993

Attest:

MICHAEL K. KIRK

*Attesting Officer*    Acting Commissioner of Patents and Trademarks